United States Patent
Lovewell (10) Patent No.: US 6,855,141 B2
(45) Date of Patent: Feb. 15, 2005

(54) METHOD FOR MONITORING IMPEDANCE TO CONTROL POWER AND APPARATUS UTILIZING SAME

(75) Inventor: James G. Lovewell, San Leandro, CA (US)

(73) Assignee: Medtronic, Inc., Minneapolis, MN (US)

( * ) Notice: Subject to any disclaimer, the term of this patent is extended or adjusted under 35 U.S.C. 154(b) by 94 days.

(21) Appl. No.: 10/201,424

(22) Filed: Jul. 22, 2002

(65) Prior Publication Data

US 2004/0015161 A1 Jan. 22, 2004

(51) Int. Cl.⁷ .............................................. A61B 18/18
(52) U.S. Cl. ........................................ 606/34; 606/41
(58) Field of Search ............................ 606/32–34, 41, 606/42, 101, 102; 607/101, 102

(56) References Cited

U.S. PATENT DOCUMENTS

| | | | | |
|---|---|---|---|---|
| 4,474,179 A | * | 10/1984 | Koch ........................... | 606/40 |
| 5,370,675 A | * | 12/1994 | Edwards et al. ............ | 607/101 |
| 5,385,544 A | | 1/1995 | Edwards et al. ............. | 604/22 |
| 5,496,312 A | * | 3/1996 | Klicek ......................... | 606/34 |
| 5,549,644 A | | 8/1996 | Lundquist et al. ........... | 604/22 |
| 5,558,671 A | * | 9/1996 | Yates ........................... | 606/38 |
| 5,817,093 A | * | 10/1998 | Williamson et al. ......... | 606/50 |
| 5,954,717 A | * | 9/1999 | Behl et al. ................... | 606/34 |
| 5,964,756 A | | 10/1999 | McGaffigan et al. ........ | 606/41 |
| 6,409,722 B1 | * | 6/2002 | Hoey et al. .................. | 606/34 |
| 6,638,275 B1 | | 10/2003 | McGaffigan et al. ........ | 606/41 |

* cited by examiner

*Primary Examiner*—Michael Peffley
(74) *Attorney, Agent, or Firm*—IPLM Group, P.A.

(57) ABSTRACT

A method for monitoring the impedance in a circuit coupling a radio frequency electrode to a radio frequency generator to control the power supplied by the generator to the electrode during a treatment procedure. In the method, the impedance in the circuit is monitored over a length of time. An expected impedance at the end of the treatment procedure is calculated from the monitored impedance and compared to a predetermined maximum impedance. The power supplied to the circuit is reduced if the expected impedance is greater than the predetermined maximum impedance. A computer-readable memory and apparatus utilizing the method are provided.

16 Claims, 6 Drawing Sheets

METHOD FOR MONITORING IMPEDANCE TO CONTROL POWER AND APPARATUS UTILIZING SAME

FIELD OF THE INVENTION

This invention pertains generally to methods and apparatus for treating tissue and, more particularly, to methods and apparatus for treating tissue utilizing radio frequency energy.

BACKGROUND

Medical devices have been provided for treating tissue of a mammalian body by the use of radio frequency energy. See, for example, U.S. Pat. Nos. 5,370,675, 5,385,544 and 5,549,644. Radio frequency energy passing from an electrode of such a device through the adjoining tissue causes heating of the tissue. In a monopolar device, the radio frequency energy passes from the active electrode to an indifferent electrode typically in contact with the exterior of the body of the patient. In order to cause desired tissue ablation and subsequent necrosis, the treated tissue is heated to a temperature in excess of approximately 47° C. However, if the temperature of the tissue being treated is elevated too high, dehydration and later charring of the tissue can occur. Such dehydration and charring can increase the impedance of the tissue to a level that prohibits radio frequency from traveling through the tissue. In view of the foregoing, prior systems have monitored the impedance of the active electrode circuit and adjusted the radio frequency power supplied to the electrode in response to such impedance measurements.

It would be desirable to provide a method and apparatus that is able to predict whether the impedance of an active electrode circuit will exceed a predetermined level during a procedure and adjust the power supplied to such circuit so that such predetermined level of impedance is not reached during the procedure.

SUMMARY OF THE INVENTION

A method is provided for monitoring the impedance in a circuit coupling a radio frequency electrode to a radio frequency generator to control the power supplied by the generator to the electrode during a treatment procedure. In the method, the impedance in the circuit is monitored over a length of time. An expected impedance at the end of the treatment procedure is calculated from the monitored impedance and compared to a predetermined maximum impedance. The power supplied to the circuit is reduced if the expected impedance is greater than the predetermined maximum impedance. A computer-readable memory and apparatus utilizing the method are provided.

DESCRIPTION OF THE INVENTION

Figure 1:
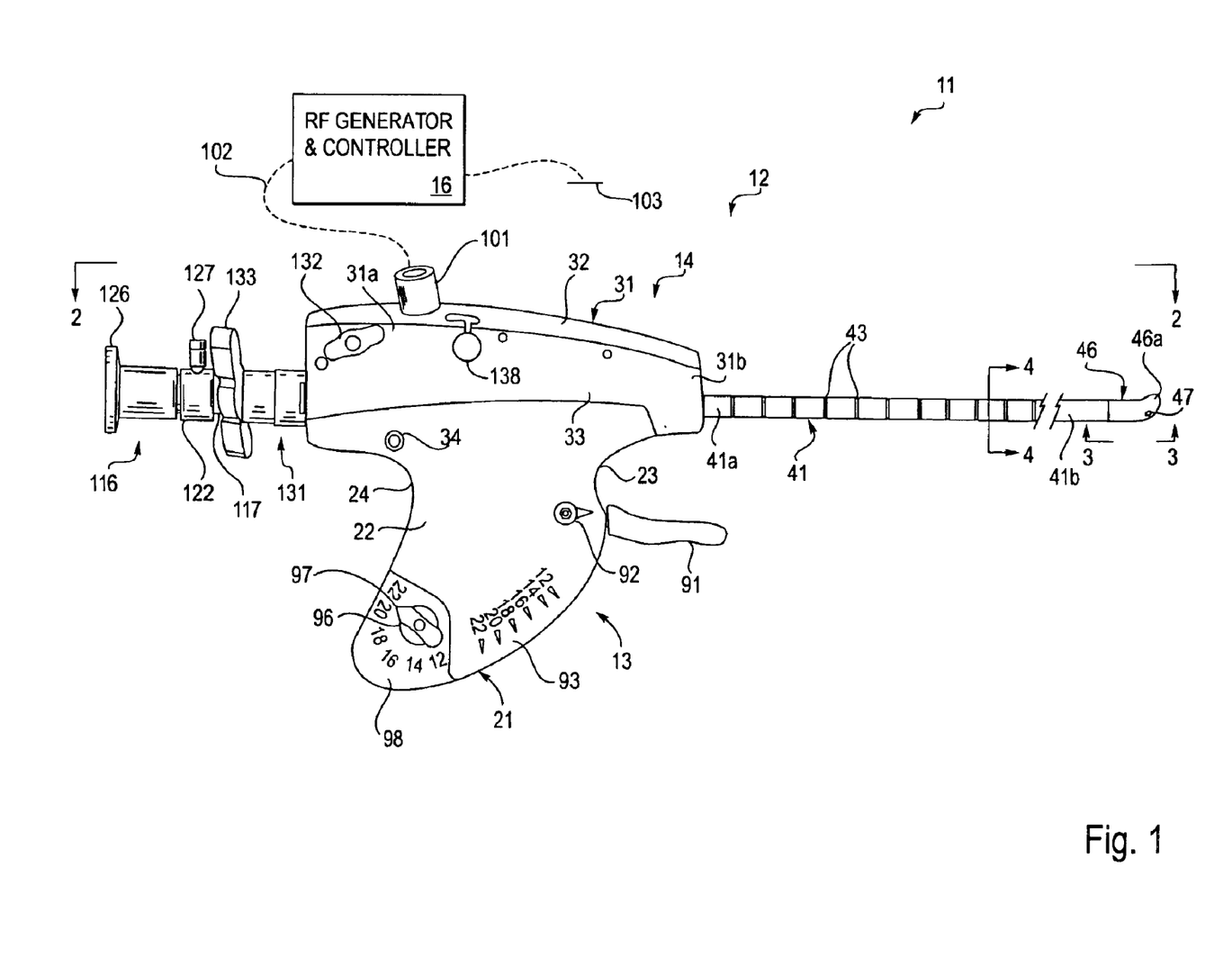
FIG. 1 is a side elevational view of an apparatus and system utilizing the method for calculating impedance of the present invention.

The method and apparatus of the present invention are for treating a mammalian body, such as a human patient. Such apparatus is part of a system 11 and can be in the form of a transurethral needle ablation apparatus or device 12 similar to the apparatus shown in U.S. Pat. No. 5,964,756 and in U.S. patent application Ser. No. 09/684,376 filed Oct. 5, 2000, the entire content of each of which is incorporated herein by this reference. Device 12 includes a reusable handle 13 on which there is mounted a detachable cartridge 14. The needle electrodes of the device are supplied with radio frequency energy from a radio frequency generator and controller 16, which can be similar to the type commercially available from Medtronic, Inc. of Minneapolis, Minn. The device 12 is further supplied with a conductive liquid such as a saline solution provided from one or more reservoirs and preferably from a saline supply 17 (see FIG. 2). Controller 16 is preferably coupled to the saline supply 17 to control the output thereof. The method and apparatus of the present invention can be utilized to monitor the impedance in the electrode circuits so as to control the amount of radio frequency energy supplied to the needle electrodes of the apparatus.

Apparatus 12 is similar in construction to the apparatus disclosed in U.S. Pat. No. 5,964,756. Using that same construction, handle 13 is comprised of a housing 21 which is ergonomically shaped so as to be adapted to fit in a human hand. Specifically, the handle 13 is in the form of a pistol grip which has a main body portion 22 that is provided with a forward indentation 23 adapted to receive the index finger of the human hand grasping the handle 13 and a larger rearwardly facing indentation 24 adapted to receive the thumb of the same human hand. Housing 21 is made from metal or any other suitable material.

Cartridge 14 consists of a cover 31 that is generally U-shaped in cross section and is formed of a suitable material such as plastic. The cover 31 is provided with proximal and distal extremities 31a and 31b and is formed by a curved top wall 32 and depending adjoining spaced-apart parallel side walls 33. A release button 34 is provided on each of the opposite sides of the housing 21 for releasing the removable cartridge 14 from the handle 13.

An elongate tubular member or probe 41 preferably in the form of a rigid torque tube made from any suitable material such as stainless steel is provided and includes proximal and distal extremities 41a and 41b. Probe 41 has its proximal extremity mounted to the distal extremity 31b of cover 31. The tubular torque member 41 has a suitable diameter as for example 18.5 French and is provided with a passage 42 circular in cross section extending therethrough (see FIG. 3). The outer surface of the probe 41 is provided with spaced-apart markings 43 which are spaced apart by one centimeter increments to aid the physician in insertion of the probe 41 into the urethra.

A bullet-shaped tip or distal guide housing 46 formed of a suitable plastic transparent to light is secured to the distal extremity of the torque tube or probe 41 in the manner described in U.S. Pat. No. 5,964,756 (see FIGS. 1 and 3). As shown in FIG. 1, the distal tip 46 has an upturned rounded portion 46a. The elongate probe 41 and the tip 46 preferably have a combined length of approximately 9.5 inches. A pair of circumferentially spaced-apart holes 47 and 48 are provided on the underside of the bullet-shaped tip 46 opposite the upturned portion 46a. The first and second holes 47 and 48 are spaced apart from each other by a suitable distance as for example one centimeter, which dimension is determined by the diameter of the torque tube 46 (see FIG. 3). First and second angled guide tubes 51 and 52 which are aligned with the respective first and second holes 47 and 48 have L-shaped 90° bends therein that are molded into the transparent bullet-shaped tip 46. Such 90° bends provided in the first and second angled guide tubes provide transitions from movement through the tubes along a longitudinal axis to movement along a transverse axis extending at 90° with respect to the longitudinal axis.

Figures 2, 3:
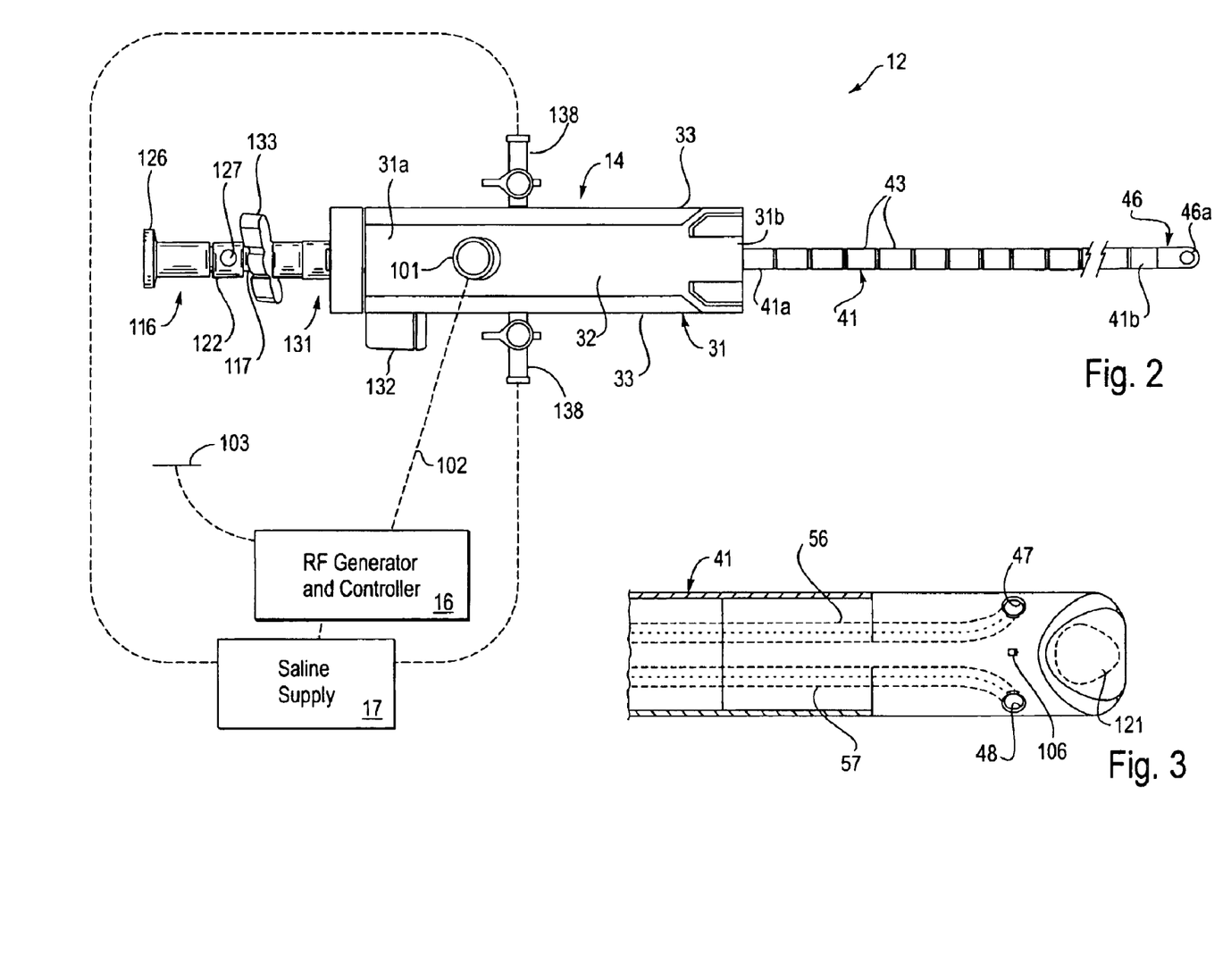
FIG. 2 is a top elevational view of the apparatus and system of FIG. 1 taken along the line 2—2 of FIG. 1.
FIG. 3 is a bottom elevation view of a portion of the apparatus of FIG. 1 taken along the line 3—3 of FIG. 1.
Figure 4:
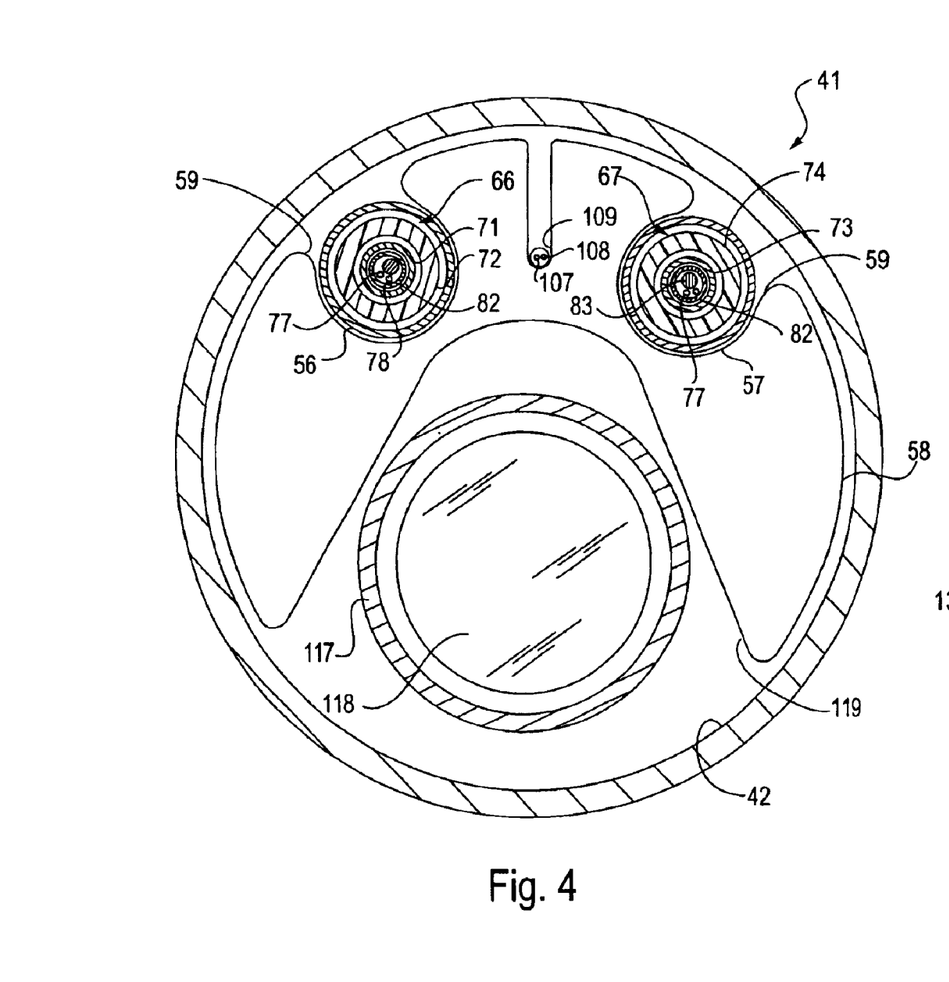
FIG. 4 is a cross-sectional view of the apparatus of FIG. 1 taken along the line 4—4 of FIG. 1.

The first and second angled guide tubes 51 and 52 adjoin straight guide tubes 56 and 57, respectively, which extend through the passage 42 provided in the torque tube or elongate probe 41 (see FIGS. 3 and 4). Each of the straight guide tubes 56 and 57 has a proximal extremity attached to cover 31 and a distal extremity attached to the distal tip 46. As shown particularly in FIG. 4, the straight guide tubes 56 and 57 are supported in predetermined spaced-apart positions in the passage 42 by an insert 58 formed of plastic that is disposed in the torque tube 41 and has spaced-apart recesses 59 formed in the outer periphery of the insert 58. The straight guide tubes 56 and 57 are made from plastic or any other suitable material.

Figure 5:
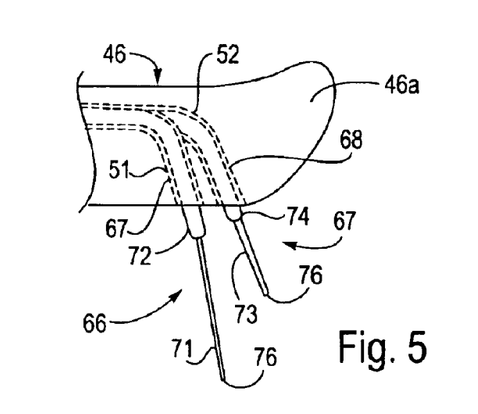
FIG. 5 is an enlarged view of the distal extremity of the apparatus of FIG. 1 wherein the first and second stylets of the apparatus are partially deployed.
Figure 6:
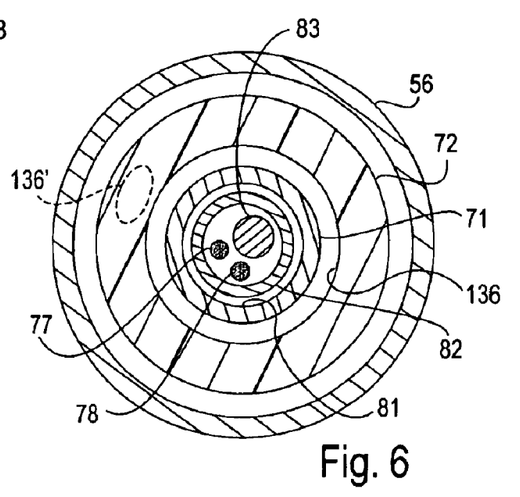
FIG. 6 is an enlarged cross-sectional view of a portion of the apparatus shown in FIG. 4.

A pair of first and second elongate members or stylets 66 and 67 are slidably mounted in the first and second straight guide tubes 56 and 57 within probe 41 (see FIGS. 4–6). Each of the elongate stylets has a proximal extremity, not shown, disposed in cover 31 and a distal extremity 68 disposed in the distal extremity of probe 41 and tip 46. First stylet 66 is preferably formed from a needle electrode 71 and a layer of insulating material disposed around the needle electrode but exposing a distal portion of the needle electrode. The layer of insulating material is preferably a sleeve 72 slidably mounted on the needle electrode 71. Second stylet 67 is similar in construction to the first stylet 66 and includes a needle electrode 73 and a sleeve 74 slidably mounted on the needle electrode 73. The needle electrodes 71 and 73 are preferably formed of a hollow superelastic nickel-titanium material having an outside diameter of 0.018 inch and an inside diameter of 0.012 inch and a wall thickness of 0.003 inch. The sleeves 72 and 74 are preferably made from plastic or any other suitable insulating material and extend through the guide tubes 51, 52, 56 and 57 so that the entire lengths of the needle electrodes 71 and 73 extending through the passage 42 are insulated from each other and from the torque tube 41. The sheaths or sleeves 72 and 74 additionally provide stiffness to the needle electrodes during penetration of the urethral or other passage wall into which tip 46 is introduced. The insulating sheaths are sized in length so that when the needle electrodes are retracted within the bullet-shaped tip 46, they are substantially covered with the insulation. When the needle electrodes are deployed, the sheaths 72 and 74 continue to cover the needle electrodes, but permit the distal portion of the needle electrodes to be exposed in the targeted tissue. The stylets 66 and 67 have an included angle of approximately 40°.

A suitable temperature sensor is optionally carried by each of the first and second stylets 66 and 67. The distal extremity of each of the needle electrodes is provided with a sharpened tip and has a thermocouple 76 or other suitable temperature sensor mounted within the sharpened tip (see FIG. 5). Each thermocouple is provided with a pair of wires 77 and 78 which extend proximally from the sharpened tip through a longitudinal lumen 81 provided in the hollow needle electrode 71 or 73 (see FIGS. 4 and 6). A separate insulating sleeve 82 is provided in each electrode lumen 81 to provide additional insulation isolating the thermocouple wires from the metal needle electrode. In order to strengthen the needle electrodes 71 and 73 and to inhibit wall collapse and kinking during bending, a nickel-titanium rod 83 is disposed within each internal sleeve 82 alongside the thermocouple wires 77 and 78. Strengthening rod 83 has an external diameter of 0.006 inch and each of the thermocouple wires 77 and 78 has an outside diameter of 0.005 inch. The rod 83 and the thermocouple wires 77 and 78 are cemented in place by a suitable polyurethane adhesive (not shown).

Handle 13 and cartridge 14 are provided with internal mechanisms much the same as described in U.S. Pat. No. 5,954,756, wherein the operation of such mechanisms are described in detail. In general, such mechanisms are adapted to be operated by a needle and sheath deployment and retraction trigger 91 that is adapted to be engaged by the forefinger of the hand holding the body portion of the housing 21 (see FIG. 1). The trigger 91 is adapted to be moved from a "load" position indicated by the arrow 92 through a plurality of deployed positions indicated by indicia 93 ranging from 12 to 22 millimeters provided on opposite sides of the housing 21. In this regard, actuation of the trigger 91 initially causes the first and second stylets 66 and 67 to slidably deploy from respective guide tubes 51 and 56 and 52 and 57 so as to extend sidewise in unison from the distal tip. Further downward movement of the trigger 91 causes the insulating sleeves 72 and 74 to retract a predetermined amount relative to the respective needle electrodes 71 and 73. The length of the resulting tissue penetration of stylets 66 and 67 is determined by the position of an interconnected pair of knobs 96, which set stops for limiting movement of the trigger 91 so that overtravel beyond the setting provided by the knobs 96 cannot occur. The interconnected knobs 96 are provided on opposite sides of the housing 21 adjacent the lower extremity of the body 21 and have pointers 97 movable over indicia 98 ranging from 12 to 22 millimeters in the same increments as the indica 93. The indicia 98 indicate the length of penetration of the needle electrodes 71 and 73, for example through the urethral wall and into the prostatic tissue of the prostate. Sleeves or sheaths 72 and 74 are retracted a predetermined amount as for example six millimeters relative to the needle electrodes so that there is exposed approximately six millimeters of the needle electrodes in the targeted tissue with the insulating sheaths still extending through the urethral or other passage wall so as to protect such wall during RF ablation of the targeted tissue.

Generator and controller 16 is electrically coupled to the first and second stylets 66 and 67, and specifically to the first and second needle electrodes 71 and 73. In this regard, an electrical connector 101 is provided on cover 31 for permitting electrical communication between the generator 16 and the proximal extremity of the needle electrodes. Controller 16 is electrically coupled to connector 101 by means of a cable 102 or other suitable lead. The generator 16 is provided with two channels of radio frequency energy, making it possible to deliver different amounts of power to two or more different needle electrodes which are typically operated in a monopolar fashion utilizing a return or dispersive electrode 103 which can be adhered to exterior of the body of the patient, for example the small of the back of the patient. The proximal ends of first and second thermocouple wires 77 and 78 are also electrically coupled to connector 101 for permitting controller 16 to monitor temperatures sensed thereby.

An optional temperature sensor such as a thermocouple 106 is preferably encapsulated in the bullet-shaped tip 46 and, as shown in FIG. 3, is disposed in the vicinity of stylet openings 47 and 48 provided in the tip. Thermocouple 106, which permits the sensing of urethral wall temperatures, is connected to wires 107 and 108 extending through the passage 42 and is supported in a recess 109 in the insert 58 (see FIG. 4). The wires 107 and 108 are electrically connected within cover 31 to connector 101 for permitting the monitoring of the readings obtained thereby by generator and controller 16. The thermocouple 106 is used to ensure that the highest temperature reached in the urethra does not exceed approximately 47° C. Such hottest location is typically found between the needle pairs 71 and 73 and it is for this reason that the thermocouple 106 is so located.

The cover 31 and the torque tube 41 are preferably sized to receive an optional telescope or scope 116 of a conventional type which includes a tubular member 117 having a rod lens 118 and fiber optics (not shown) surrounding the rod lens (see FIGS. 1 and 2). The scope 116 is movable through the cover 31 and a recess 119 provided in the insert 58 disposed in the passage 72 of the tube 41 and thence into a bore 121 provided in the bullet-shaped tip 46 (see FIG. 3). The bore 121 is in alignment with the recess 119 provided in the torque tube 41. When the distal extremity of the tubular member 117 is positioned within the bore 121, it is possible to view the surrounding region through the transparent tip 46 because the tip 46 has an index of refraction which is similar to the surrounding liquid, such as saline solution, within the urethra or other body passage into which probe 41 has been placed. A fitting 122 is provided on the proximal extremity of the tubular member. 117 and includes an eyepiece 126 and a connector 127 for making connection to a fiber optic light source (not shown).

In order to permit movement of the scope 116 into position so that the physician can also observe independently deployment of the first and second needle electrodes 71 and 73, optional means is preferably provided for causing longitudinal movement of the scope 116 relative to the torque tube 41 (see FIGS. 1 and 2). To this end telescope moving means 131, described in detail in copending patent application Ser. No. 09/684,376 filed Oct. 5, 2000 is provided in the proximal extremity 31 a of cover 31. In general, the telescope moving means 131 includes a telescope positioning knob 132 extending from one of the side walls 33 of cover 31 and a scope locking lever 133. Release button 34, and the internal mechanisms and operation thereof, are also described in copending patent application Ser. No. 09/684, 376 filed Oct. 5, 2000.

Each of the first and second stylets 66 and 67 optionally has a lumen extending from the proximal extremity to the distal extremity of the stylet for permitting a conductive or other fluid to be introduced by apparatus 12 into the tissue being treated. The lumen can be provided in any portion of the stylet and can be in the form of a lumen extending through the needle electrode or through the insulating sleeve. In one preferred embodiment, and as shown in the drawings, each of the insulating sleeves 72 and 74 is provided with a lumen 136 extending longitudinally therethrough. As shown in FIG. 6, the lumen can be an annular lumen 136 extending around the respective needle electrode and permitted by sizing the internal diameter of the insulating sleeve larger than the external diameter of the needle electrode. Alternatively, or in addition, the lumen can be in the form of one or more lumens 136', one of which is shown in dashed lines in FIG. 6, which are offset from the central lumen of the sleeve 72. Where more than one lumen 136' is provided, such lumens can be spaced circumferentially or otherwise about the insulating sleeve.

The lumen 136 is accessible from the proximal extremity of the respective stylet and a reservoir 17 of a suitable conductive liquid such as saline is coupled to the proximal extremity of each stylet for supplying such liquid to the tissue targeted by apparatus 12 (see FIG. 2). One or more suitable fluid connectors 138 are provided on apparatus 12 for permitting fluid communication between reservoir or saline supply 17 and sleeve lumens 136. In the illustrated embodiment of the invention, first and second fluid connectors in the form of first and second stopcocks 138 extend from the opposite side walls 33 of the cover 31 and connect to saline supply 17 by means of suitable lines or tubing, shown in dashed lines in FIG. 2.

Figure 7:
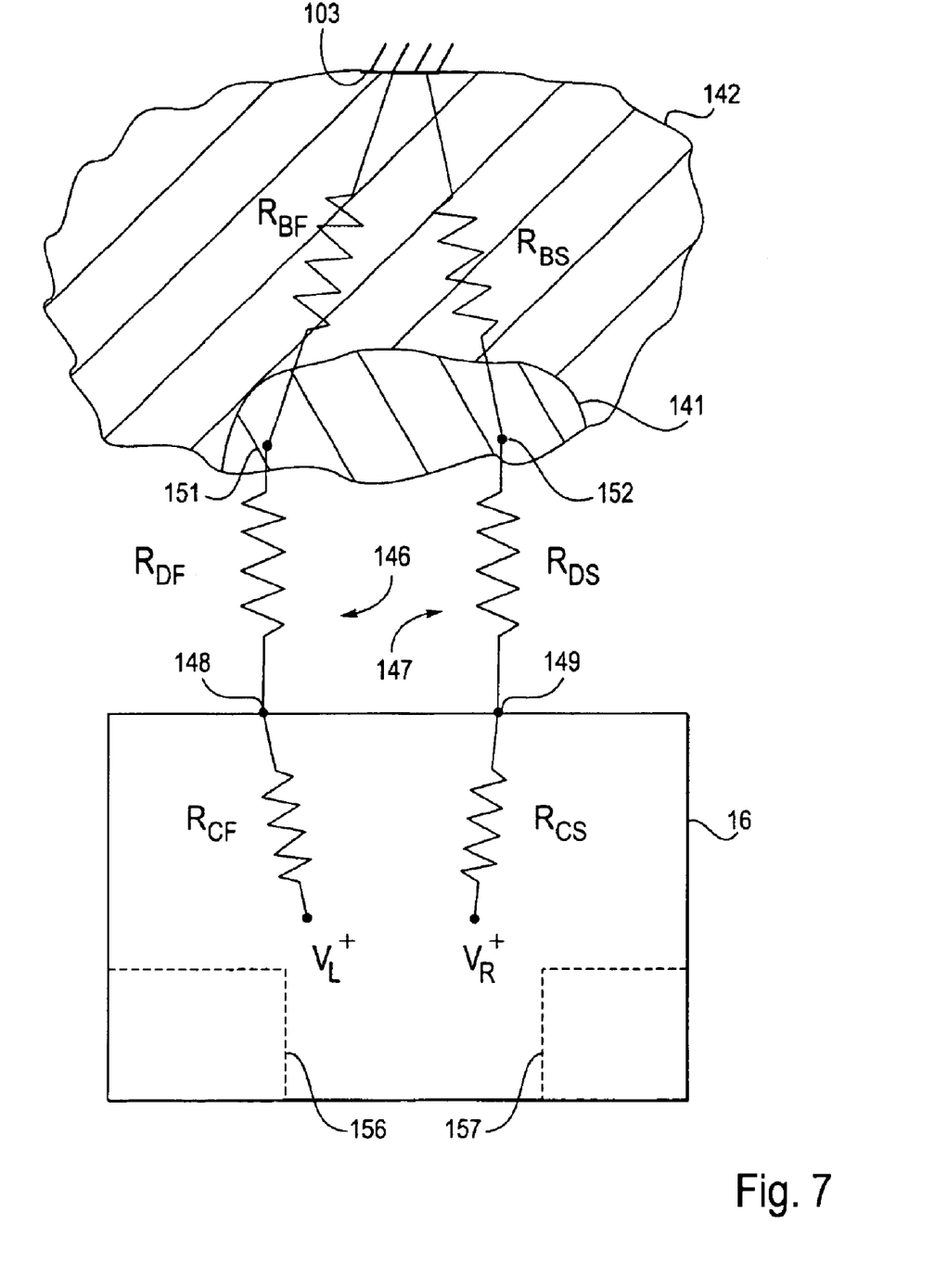
FIG. 7 is a circuit diagram of the radio frequency electrodes of the apparatus of FIG. 1 when disposed in tissue being treated.

A circuit diagram of system 11 when first and second stylets 66 and 67 are exposed in tissue targeted for treatment is shown in FIG. 7, where targeted tissue 141 of a mammalian body 142 are also depicted. In general, first circuit 146 therein depicts the electrical circuit created by controller 16, cable 102, apparatus 12 and body 142 of the patient pertaining to first stylet 66 and extending from the voltage source $V_F^+$ for such stylet 66 within controller 16 to the return or indifferent electrode 103 preferably adhered to the back side of the patient. Similarly, second circuit 147 depicts the electrical circuit created by controller 16, cable 102, apparatus 12 and body 142 pertaining to second stylet 67 and extending from the voltage source $V_S^+$ to the disbursive electrode 103. Second circuit 147 is distinct from first circuit 146 in that there is no physical connection between such circuits. Nodes 148 and 149 respectively refer to the locations where first and second circuits 146 and 147 connect through cable 102 to controller 16. Nodes 151 and 152 respectively refer to the exposed portions of first and second needle electrodes 71 and 73 within the targeted tissue 141.

The impedance for first circuit 146 within controller 16 is depicted by reference $R_{CF}$ in FIG. 7. The impedance between node 148 and node 151 is depicted by reference $R_{DF}$ and the impedance of body 142, that is between node 151 and return electrode 103, is depicted by reference $R_{BF}$. Similarly, second circuit 147 has respective impedance components $R_{CS}$, $R_{DS}$, and $R_{BS}$.

Controller 16 includes a central processing unit or central processor 156 and a computer memory 157 electrically coupled to such central processor or CPU 156. Computer-readable memory 157 includes a program for performing the method of the present invention, which is set forth in the flow chart of FIG. 8 and described below.

In one method for treating tissue of the present invention, system 11 can be used to treat benign prostatic hyperplasia in a human male prostate. In such a procedure, the targeted tissue 141 is the prostatic tissue of a prostate. A suitable procedure for treating a prostate of a human male is described in detail in U.S. Pat. Nos. 5,549,644 and 5,964,756, the entire contents of which are incorporated herein by this reference. In general, the distal extremity of torque tube 41 of apparatus 12 is introduced through the penis into the urethra until distal tip 46 is in the vicinity of the prostate. The operating physician then pulls down on trigger 91 to cause the first and second stylets 66 and 67 to deploy from distal tip 46. The sharpened tips of first and second needle electrodes 71 and 73 penetrate the urethral wall to permit the stylets to extend into the prostatic tissue 141 to be treated. As discussed above, further downward movement of trigger 91 causes first and second sleeves 72 and 74 to retract relative to the electrodes. The sleeves, however, extend through the urethral wall so as to protect the wall from radio frequency energy supplied to the needle electrodes 71 and 73.

If the operating physician desires to create a wet electrode within the prostatic tissue 141, a procedure such as described in cop-ending U.S. patent application Ser. No. 10/201,502, filed Jul. 22, 2002, published as Publication No. US2004/0015162 A1, the entire content of which is incorporated herein by this reference, can be utilized. In general, a conductive liquid provided by supply 17 is introduced through first and second stylets 66 and 67 into the prostatic tissue 141 to form such a wet electrode about each of the first and second stylets 66 and 67. The exterior surface of each such wet electrode serves as an outer electrode surface from which radio frequency energy is delivered.

Figure 10:
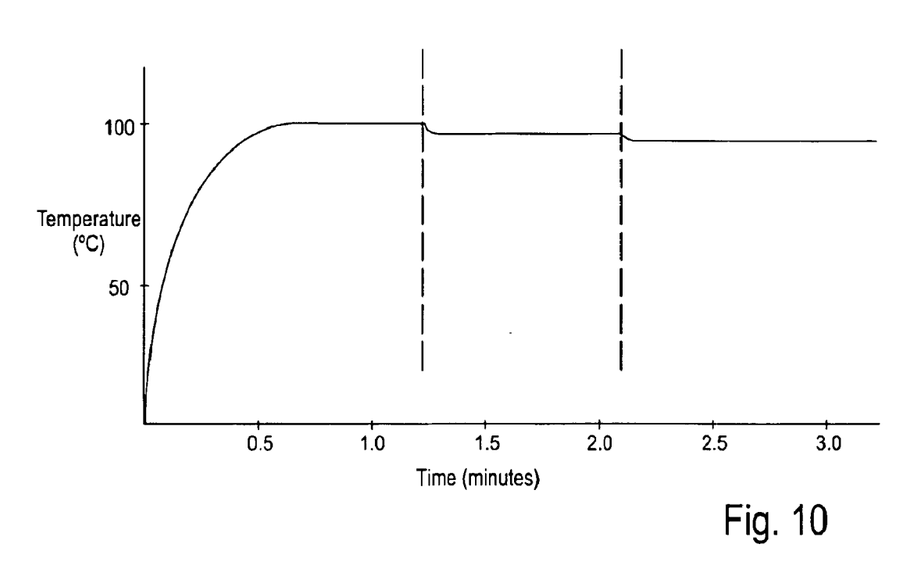
FIG. 10 is a graph of temperature versus time in a procedure utilizing the method of FIG. 8 and the apparatus and system of the present invention.

Radio frequency energy is supplied by radio frequency generator and controller 16 to first and second needle electrodes 71 and 73 to create lesions in the prostatic tissue 141 by ablating the tissue. The method of the invention set forth in FIG. 8 applies to both electrodes 71 and 73 but, for simplicity, is described with respect to only one of the electrodes. Step 161 corresponds to the initial supply of radio frequency energy to such electrode 71 or 73. The amount of power so supplied to the electrode can be predetermined or estimated to raise the temperature of the prostatic tissue above 47° C. and preferably to approximately 110° C., as shown in FIG. 10. Although the power can be ramped over time to such predetermined power level, in one preferred embodiment the power is raised from zero to such predetermined power level in a stepwise fashion. A suitable initial power applied to each of the electrodes 71 and 73 in such stepwise fashion has been found to be 15 watts.

Figure 8:
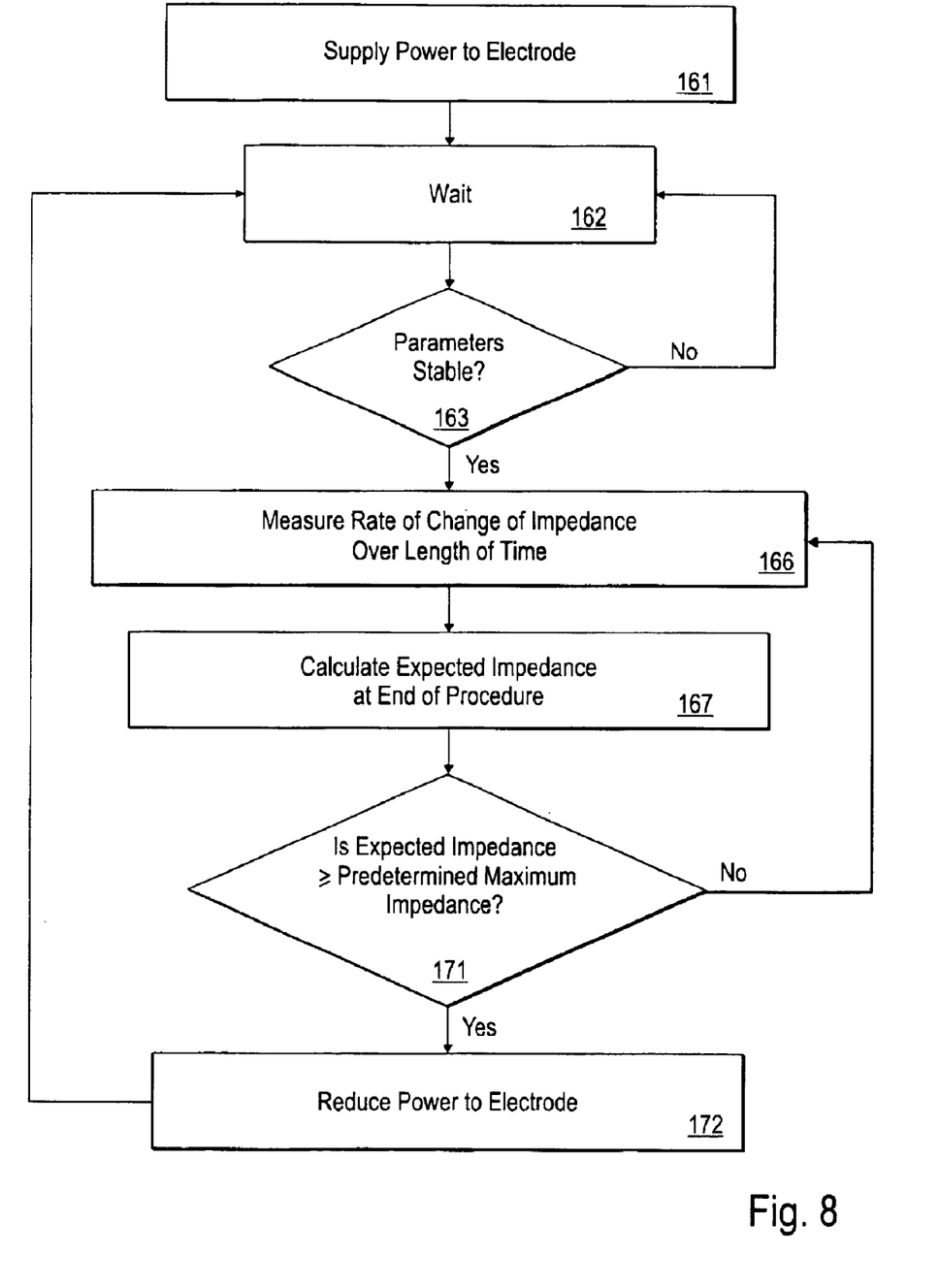
FIG. 8 is a flow chart of the method for monitoring impedance to control power of the present invention.

In step 162 set forth in FIG. 8, controller 16 and the operator thereof wait for a length of time for certain parameters of the procedure, such as the temperature of the targeted tissue 141, to stabilize. As shown in the exemplary data contained in FIG. 10, the temperature of the prostatic tissue rises to the desired temperature of 110° C. in approximately 30 or 40 seconds. The length of such wait is dependent, at least in part, on the amount of the electrode 71 or 73 that is disposed in the targeted tissue. Such amount of exposed surface, dependent on the diameter and length of the exposed portion of the electrode, is relevant in determining the current density at the surface of the electrode. The smaller the current density, the longer it takes to heat the tissue 141 to the targeted tissue for a given power. The temperature sensed by the thermocouple 76 in each of the first and second needle electrodes 71 and 73 can be displayed on a meter or other visual display on controller 16.

Figure 9:
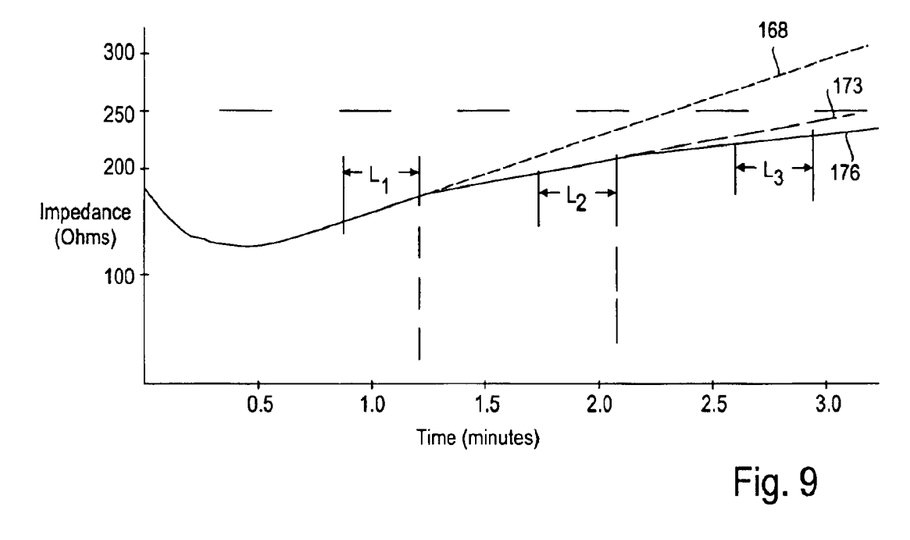
FIG. 9 is a graph of impedance versus time in a procedure utilizing the method of FIG. 8 and the apparatus and system of the present invention.

The impedance of the first and second circuits 146 and 147 is similarly monitored during the wait of step 162. In one preferred method of the invention, particularly where cross talk exists between adjacent electrodes disposed in the targeted tissue, the impedance is monitored by the method set forth in copending U.S. patent application Ser. No. 10/201,401, filed Jul. 22, 2002, now U.S. Pat. No. 6,730,079. As shown in FIG. 9, the impedance in the circuit 146 or 147 decreases during the initial portion of the procedure. This is due to the breaking down or bursting of some prostatic cells. The resulting release of fluid from these cells increases the hydration of the targeted tissue 141. Accordingly, the decrease in impedance at the start of the procedure results from a decrease in $R_{BF}$ or $R_{BS}$, that is the portion of the impedance between the respective needle electrode 71 or 73 and the indifferent electrode 103. Thereafter, it has been found that in some procedures the impedance of the targeted tissue 141 increases at a substantially constant rate throughout the procedure when the temperature of such tissue is maintained at a constant temperature such as 110° C. or below. Controller 16 can include a meter or other visual display thereon for showing the measured impedance in each of first and second circuits 146 and 147.

In decision step 163 shown in FIG. 8, controller 16 determines whether certain parameters of the procedure have stabilized after the wait of step 162. For example, if fluctuations in the temperature of the prostatic tissue or in the impedance of the respective circuit exist after the wait of step 162, controller 16 returns to step 162 for an additional wait.

In one preferred method of the invention, the wait of step 162 lasts approximately one second and the controller travels through the loop of steps 162 and 163 until the temperature of the targeted tissue and the impedance of the electrode circuit 146 or 147 stabilize. In another preferred method of the invention, step 163 is eliminated and instead the controller waits for a predetermined period of time ranging from 20 to 60 seconds and preferably from 40 to 60 seconds in step 162 before moving directly to step 166. When step 163 is eliminated, the predetermined period of time for step 162 is set so as to be sufficient for such procedure parameters to stabilize.

Throughout the duration of the procedure, the temperature of the targeted tissue 141 is preferably maintained constant so as to facilitate an accurate prediction of the impedance expected to exist in the circuit 146 or 147 at the end of the procedure. It is preferred that such constant tissue temperature be at least 110° C. and preferably approximately 110° C. when the targeted tissue is prostatic tissue since it has been found that an undesirable increase in the impedance of the prostatic tissue occurs when the temperature approaches and exceeds approximately 125° C. When a constant tissue temperature of approximately 110° C. is maintained, it has been additionally found that an acceptable impedance level exists in many prostates to permit a relatively high current density on the electrode surface and thus a relatively rapid introduction of energy into the prostate.

Changes in the power supplied to the electrode are typically necessary to maintain the prostatic temperature at a relatively constant temperature throughout the remainder of the procedure. In this regard, controller 16 can include a program within memory 157 or be otherwise programmed to automatically reduce the radio frequency energy supplied to a needle electrode 71 or 73 in response to undesirable changes in the temperature adjacent such needle electrode. In addition, the operator can manually adjust the amount of radio frequency energy being supplied to a needle electrode in response to such temperature readings.

The program within memory 157 next directs controller 16 to move to step 166 in FIG. 8 to monitor the impedance, and specifically the change of impedance and more specifically the rate of change of impedance, in the circuit over a length of time. In FIG. 9, for example, step 166 commences at approximately 52 seconds into the procedure and the length of time, depicted by $L_1$, is approximately 20 seconds. The length of time for step 166 is of any suitable length and can range from ten to 120 seconds. As discussed above, the temperature of the targeted tissue in the vicinity of the electrode being monitored is preferably maintained constant during the measuring step 166.

In step 167 of the invention, the program within memory 157 directs controller 16 to calculate an expected impedance at the end of the treatment procedure. In the procedure set forth in FIG. 8, controller utilizes the change of impedance over time determined in step 166 to calculate the expected impedance at the end of the procedure. In the preferable situation where the rate of change of impedance over time is relatively constant, the expected impedance at the end of the procedure can be determined by extrapolation. In FIGS. 9 and 10, for example, the procedure is shown as being approximately three minutes, 15 seconds in duration. The extrapolation in step 166 is shown by line 168, which predicts an impedance of greater than 300 ohms at the end of the treatment procedure. Controller can be additionally programmed to calculate the expected impedance at the end of the treatment period by various other known algorithms such as least squares or polynomials.

In decision step 171, the expected impedance calculated in step 167 is compared to a predetermined maximum impedance. Although such predetermined maximum amount can be of any suitable value, for example between 200 and 300 ohms, it is preferably chosen to be the level at which undesirable dehydration of the targeted tissue 141 occurs. As discussed above, such dehydration inhibits if not precludes the passage of further radio frequency energy through the targeted tissue and can thus undesirably limit the size of the resulting lesion. In one preferred procedure, the predetermined maximum impedance is 250 ohms.

If controller 16 predicts in step 171 that the expected or estimated impedance in the respective circuit 146 and 147 will equal or exceed the predetermined maximum impedance at or before the end of the procedure, then the method of the present invention continues to step 172 of FIG. 8 wherein controller 16 directs that the temperature of the targeted tissue 141 be reduced. In one preferred method of the invention, the temperature is reduced 2° C. for each 20 ohms that the expected impedance exceeds 250 ohms until a minimum temperature of 98° C. is achieved. Such reduction in temperature, shown in FIG. 10 where the sensed temperature of the tissue 141 is reduced approximately 4° C. at approximately 1 minute, 12 seconds into the procedure, is accomplished by a reduction in power supplied to the needle electrode. Thereafter, the controller 16 is directed to return to step 162.

If the method of the invention predicts that the expected impedance will not equal or exceed the predetermined maximum impedance after the initial 20 second observation window of step 166, then step 171 directs controller 16 to return to step 166 and continue in the loop of steps 166, 167 and 171 so as to expand the observation window during which the change of impedance is monitored and the expected impedance at the end of the procedure calculated. Longer observation windows provide more data for the calculation of the expected impedance at the end of the procedure and thus contribute to the reliability of the predicted expected impedance. If any time during such loop the expected impedance is determined in step 171 to exceed the predetermined maximum impedance, then controller 16 moves to step 172. Alternatively, if the expected impedance from step 167 continues to remain below the predetermined maximum impedance, then the procedure continues to completion without further reductions to the temperature of the targeted tissue, accomplished by reductions in the amount of radio frequency power supplied to the needle electrode.

If the controller is directed by step 172 to return to step 162, the controller 16 waits for an interval of time for the procedure parameters to stabilize. In one preferred method of the invention, the controller is directed to wait for five seconds for the temperature of the targeted tissue and the impedance in the electrode circuit to stabilize from the reduction in power directed by step 172.

After the procedure parameters have stabilized, including instances where controller 16 returns to step 162 for an additional wait to accomplish such stabilization, the controller returns to step 166 to remeasure the rate of change of impedance in the circuit over an additional length of time, identified as $L_2$ in FIG. 9. As discussed above with respect to $L_1$, the length of time $L_2$ can be of any suitable length of time and, for example, can be a length of time equal to or different than length of time $L_1$. In the example of FIG. 9, the remeasuring of the rate of change of impedance commences at one minute, 45 seconds into the procedure and lasts approximately 20 seconds until two minutes, 5 seconds into the procedure. As shown in FIG. 10, the temperature of the targeted tissue 141 remains constant during such measurement period $L_2$.

The program within memory 157 next directs controller 16 to step 167 where a new expected impedance at the end of the treatment procedure is calculated from the remeasured rate of change of impedance previously determined in step 166. In FIG. 9, for example, the controller uses extrapolation line 173, whose slope is equal to the remeasured rate of change of impedance, to predict that the new expected impedance will be approximately 250 ohms at the end of the procedure. Thereafter, the controller moves to decision step 171 where the new expected impedance is compared to the predetermined maximum impedance discussed and utilized above. Since the new expected impedance is equal to the predetermined maximum impedance value of 250 ohms, controller 16 moves to step 172 wherein the targeted temperature is decreased resulting in a further reduction in the power to the needle electrode. Such temperature reduction appears in FIG. 10 at two minutes, five seconds into the procedure.

Steps 162, 163, 166 and 167 are further repeated by controller 16 before the controller again returns to step 171 to determine whether a further recalculated expected impedance at the end of the procedure will be greater than or equal to the predetermined maximum. In the example of FIGS. 9 and 10, controller 16 measures the rate of change of impedance over the length of time $L_3$, commencing at approximately two minutes, 38 seconds into the procedure. In step 166 the controller thereafter calculates a further new expected impedance at the end of the procedure through third extrapolation line 176 shown in FIG. 9. As can be seen from FIG. 9, the further new expected impedance ohms at the end of the procedure is less than 250 ohms and, thus, controller 16 decides in step 171 to continue in the loop of steps 166, 167 and 171 in the manner set forth above.

The procedure and apparatus of the invention desirably maintain tissue impedance at acceptable levels throughout the procedure. In doing so, hydration of the tissue is not reduced so as to inhibit the passage of radio frequency energy from a radio frequency electrode to the return electrode. The inhibition of dehydration permits relatively high temperatures to be maintained throughout the procedure. Such high temperatures contribute to reducing the time of the procedure, which is desirable to the patient.

Although the procedure and apparatus of the invention have been described in the context of procedures where the impedance increases linearly during the procedure, the procedure and apparatus of the invention can also be utilized in any procedure where the impedance can be predicted at some future time in the procedure. In this regard, step 166 can be eliminated if the expected impedance at the end of the procedure for the circuit being monitored can be calculated in another fashion, for example without the need for determining the rate of change or other change of impedance over time.

The foregoing procedure of the invention has been described with the use of first and second stylets 66 and 67, however it should be appreciated that any plurality of stylets can be utilized. Further, it should be appreciated that the apparatus and system of the present invention can be of any suitable type having at least first and second active electrodes. The method can be utilized in any such apparatus and system where the impedance of at least one of the first and second active electrode circuits is monitored and is preferably suited for an apparatus and system utilizing radio frequency energy. Although the method and apparatus of the invention have been described in connection with the treatment of the prostate, such method and apparatus can be used in any tissue of the body.

From the foregoing, it can be seen that a new method and apparatus have been provided for monitoring the impedance in a circuit coupling a radio frequency electrode to a radio frequency generator to control the power supplied to the electrode. The method and apparatus permit the impedance of the circuit to be predicted so as to determine whether the impedance is expected to remain within acceptable levels for the remaining duration of the procedure. If unacceptably high impedance levels are predicted, power to the radio frequency electrode is reduced.

What is claimed is:

1. A method for monitoring impedance in a circuit coupling a radio frequency electrode to a radio frequency generator to control power supplied by the generator to the electrode during a treatment procedure comprising the steps of monitoring the impedance in the circuit over a length of time, calculating an expected impedance at the end of the treatment procedure from the monitored impedance, comparing the expected impedance to a predetermined maximum impedance and reducing the power supplied to the circuit if the expected impedance is greater than the predetermined maximum impedance.

2. The method of claim 1 wherein the monitoring step includes the step of measuring the change of impedance over the length of time.

3. The method of claim 2 wherein the measuring step includes the step of measuring the rate of change of impedance over the length of time.

4. The method of claim 1 further comprising the step of maintaining the temperature of the tissue constant during the monitoring step.

5. The method of claim 1 further comprising the step of waiting a duration of time for procedure parameters to stabilize before commencing the monitoring step.

6. The method of claim 1 wherein the predetermined maximum impedance is between 200 and 300 ohms.

7. The method of claim 6 wherein the predetermined maximum impedance is 250 ohms.

8. The method of claim 1 further comprising the steps of remonitoring the impedance in the circuit over an additional length of time, calculating a new expected impedance at the end of the treatment procedure from the remonitored impedance, comparing the new expected impedance to the predetermined maximum impedance and reducing the power supplied to the circuit if the new expected impedance is greater than the predetermined maximum impedance.

9. The method of claim 1 wherein the radio frequency electrode is a needle electrode.

10. The method of claim 9 wherein the needle electrode is slidably carried by an elongate probe member introduceable into the urethra of a human male for treatment of the tissue of the prostate.

11. The method of claim 9 wherein a temperature sensor is carried by the needle electrode.

12. The method of claim 1 further comprising the step of performing a medical procedure on the tissue.

13. A computer-readable memory for use with a radio frequency controller and a circuit to couple a radio frequency electrode to the controller, the memory containing a computer program for causing the controller to monitor impedance in the circuit so as to control power supplied by the generator to the electrode during a treatment procedure by measuring the change of impedance in the circuit over a length of time, calculating an expected impedance at the end of the treatment procedure from the change of impedance, comparing the expected impedance to a predetermined maximum impedance and reducing the power supplied to the circuit if the expected impedance is greater than the predetermined maximum impedance.

14. The computer-readable memory of claim 13 wherein the computer program further causes the controller to remeasure the change of impedance in the circuit over an procedure from the remeasured change of impedance, compare the new expected impedance to the predetermined maximum impedance and reduce the power supplied to the circuit if the new expected impedance is greater than the predetermined maximum impedance.

15. A radio frequency controller for use with a circuit to couple a radio frequency electrode to the controller comprising a computer-readable memory containing a computer program for causing the controller to monitor impedance in the circuit so as to control power supplied by the generator to the electrode by measuring the rate of change of impedance in the circuit over a length of time, calculating an expected impedance at the end of the treatment procedure from the rate of change of impedance, comparing the expected impedance to a predetermined maximum impedance and reducing the power supplied to the circuit if the expected impedance is greater than the predetermined maximum impedance, and a central processing unit coupled to the memory for executing the program in the memory.

16. The radio frequency controller of claim 15 wherein the program in the memory further causes the controller to maintain the temperature of the tissue constant while measuring the rate of change of impedance in the circuit over the length of time.

* * * * *